United States Patent [19]

Buckley

[11] Patent Number: 4,698,848
[45] Date of Patent: Oct. 13, 1987

[54] BLOUSE FOR CARDIAC PATIENTS

[76] Inventor: Mary C. Buckley, 220 Schley St., Cumberland, Md. 21502

[21] Appl. No.: 911,998

[22] Filed: Sep. 26, 1986

[51] Int. Cl.$^4$ .................... A41D 10/00; A41D 13/00; A61B 5/05
[52] U.S. Cl. ......................... 2/114; 2/247; 2/250; 2/DIG. 7; 128/644; 128/696; 128/402
[58] Field of Search .............. 2/DIG. 7, 114, 94, 250, 2/249, 311, 312, 247; 128/696, 644, 695, 670, 402, 384, 385; 224/229, 230, 250

[56] References Cited

U.S. PATENT DOCUMENTS

| | | | |
|---|---|---|---|
| D. 236,293 | 8/1975 | Banks | 2/114 X |
| 1,092,144 | 4/1914 | Grushlaw . | |
| 1,778,057 | 10/1930 | Ballentine | 2/250 |
| 1,795,912 | 3/1931 | Walters | 2/250 |
| 2,156,504 | 5/1939 | Liss | 2/312 |
| 2,479,246 | 8/1949 | Lupo | 2/114 |
| 2,707,282 | 5/1955 | Paterson | 2/DIG. 7 |
| 3,047,877 | 8/1962 | Palazzo | 2/94 |
| 3,534,727 | 10/1970 | Roman | 128/644 |
| 4,026,278 | 5/1977 | Ricketts et al. . | |
| 4,055,855 | 11/1977 | Ragone et al. | 2/114 |
| 4,114,352 | 9/1978 | Horton et al. | 2/DIG. 7 |
| 4,266,297 | 5/1981 | Atkins | 2/2.5 |
| 4,411,267 | 10/1983 | Heyman | 128/402 X |
| 4,498,480 | 2/1985 | Mortensen | 128/644 |
| 4,507,802 | 4/1985 | Small | 2/2.5 |
| 4,570,268 | 2/1986 | Freeman | 2/DIG. 7 |
| 4,578,825 | 4/1986 | Vote | 2/DIG. 7 |

OTHER PUBLICATIONS

"Enrichments" Catalog of Enrichments, Inc., Hinsdale, Ill. (not dated) Catalog No. AQ-6765; pp. 1, 2, 38, 40, 42, 52.
"Catalog 100H", Angelica Corporation, St. Louis, Mo., (1984), pp. 1, 2, 62, 63.

Primary Examiner—Stephen Marcus
Assistant Examiner—T. Graveline
Attorney, Agent, or Firm—Saidman, Sterne Kessler & Goldstein

[57] ABSTRACT

A cardiac garment is disclosed which features front closing, an interior pocket for a monitor, a belt tying in front or in back, and closure means. It provides modesty, comfort, durability and an attractive appearance. The garment is designed for use in all cardiac rehabilitation situations including exercise and stress testing. The entire garment is made of x-ray transparent materials.

7 Claims, 3 Drawing Figures

BLOUSE FOR CARDIAC PATIENTS

FIELD OF THE INVENTION

This invention relates to blouses, and more particularly, to blouses which permit female cardiac patients to maintain modesty while permitting proper cardiac monitoring.

BACKGROUND OF THE INVENTION

During cardiac care and cardiac rehabilitation, patients are subject to frequent examinations of the chest area, especially for attachment of electrodes to which are connected heart monitors for measuring the strength of the heart under a variety of circumstances. Up until now, very little thought or consideration have been given to the personal needs of the female cardiac patient, whose modesty presents an entirely different set of problems from that of the male patient.

For example, while males can be stress tested bare chested, female cardiac patients required to take stress tests have very few choices of torso-covering clothing, none of which are suitable. The options known to the present inventor include the standard hospital gown, which is too long for many female patients and, since it opens in the rear, provides no access to the chest area. Moreover, most hospital gowns tend to be very bulky, since they have to fit a wide variety of patients. This renders them ugly and uncomfortable, particularly during exercise. To simply wear a brassiere provides little advantage with respect to modesty. Webbing cover-ups are also used, but these are expensive single-use garments which tend to be constricting and uncomfortable.

A further difficulty with most of the clothing available to cardiac patients is posed by the fact that patients in high-level cardiac care frequently must wear a transmitter connected to electrodes that are attached to the torso. Males can carry the transmitter in a pocket of their pajamas or the like. At present, female patients typically wear the transmitter in a pouch suspended from the neck like a necklace by cloth straps secured by "VELCRO" brand closures (synthetic materials which adhere when pressed together). Alternatively, the transmitter is wrapped in a cloth and pinned to the gown or put in a belt with a pouch. Each of these possibilities is awkward. If a female patient allows the transmitter to hang loose on a necklace, the weight frequently pulls the electrodes off. Furthermore, the "VELCRO" brand closures that are used to secure the cloth straps often catch in the patient's hair or earrings. If the transmitter is pinned to the gown, it pulls on the garment causing discomfort and poor fit. The belt alternative is uncomfortable and inconvenient.

These difficulties are particularly exacerbated when the transmitter and electrodes must be worn during rehabilitative exercise, as is common.

The Angelica Corp. of St. Louis, Missouri makes an intensive care unit "(ICU)" gown which includes VELCRO brand closures for the back and on the sleeves, and which includes a "telemetery [sic] pocket . . . located on the center chest portion of the gown." This gown would appear to have been developed in response to some of the same concerns which motivated Applicant's invention. However, the Angelica gown is not form-fitting, is unattractive, and is evidently intended for "one-size-fits-all" use (as it is available only in large size). The placement of the pocket on this gown is not optimal. To have the telemetry equipment resting directly on the patient's chest is undesirable. Even if this location were generally acceptable, it would not suit all patients due to their variation in size. Nor would a gown of this type be suitable for exercise, as to fit all patients it would have to be must too big for most of them. Furthermore, the Angelica gown does not provide ready front access, needed to place and check on the monitoring electrodes.

OBJECTS OF THE INVENTION

One object of the present invention is to provide a garment for stress testing and related cardiac care which provides modesty, allows a doctor easy access to the chest, is reusable, and is generally more comfortable for the female patient.

Another object of the present invention is to provide a garment with an internal pocket and belt that can easily and comfortably secure a cardiac monitor.

Another object of the present invention is to provide a front closing garment meeting the objects of the invention listed above and which is x-ray penetrable, so that an x-ray of a patient's torso can be accomplished without removal of the garment.

Another object of the present invention is to provide a garment that allows for comfortable carrying and security of a cardiac monitor during a female patient's entire cardiac rehabilitation period, including exercise.

It is a further object of the present invention to provide a garment that gives an attractive appearance, as well as comfort and durability, which is suited for all activities of the patient's typical day, including examination, exercise, stress testing, resting, and hobby or other recreational activities, while allowing selectively adjustable fit, so that each patient need not be separately fitted with the garment.

The above and other objects and advantages of this invention will become more readily apparent when the following description is read in conjunction with the accompanying drawings.

SUMMARY OF THE INVENTION

The above needs of the art and objects of the invention are satisfied by the present invention which is a front closing garment for cardiac patients comprising x-ray penetrable closures, an interior front pocket for a cardiac monitor, a body portion, and a belt capable of being tied in the front or the back to secure the monitor and provide adjustable fit. In a preferred embodiment the garment has short sleeves so as not to interfere with the blood-pressure testing.

DETAILED DESCRIPTION OF A PREFERRED EMBODIMENT

Figure 1:
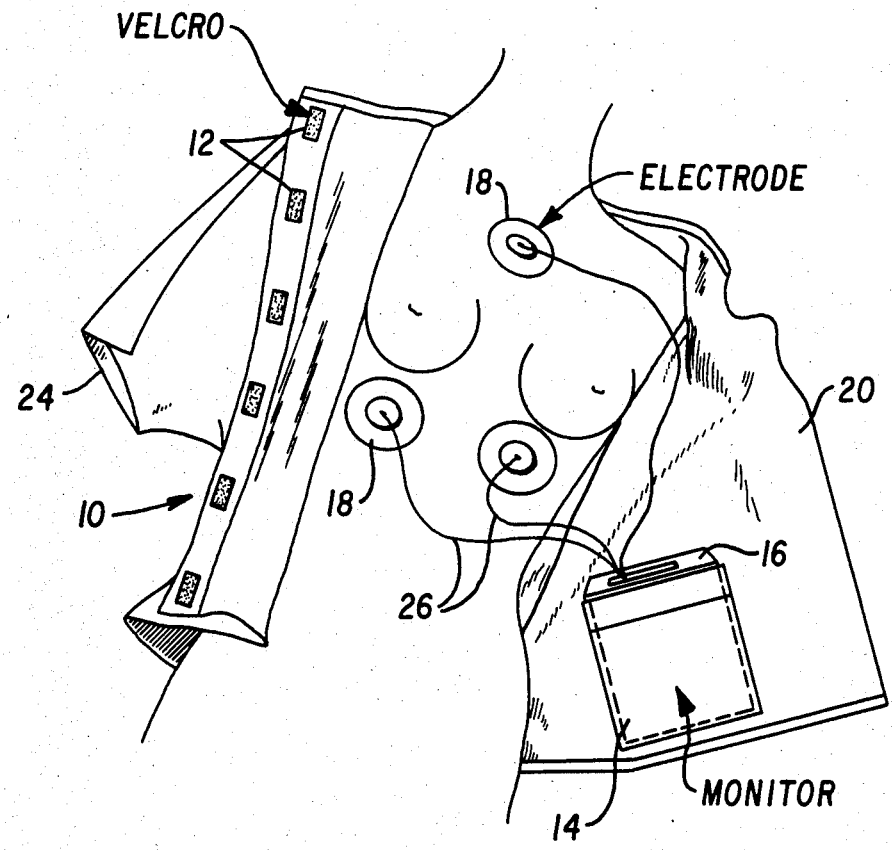
FIG. 1 is a frontal view of the garment of the present invention in an open configuration revealing the interior structure.

Referring now to the drawings and, in particular, to FIG. 1, a garment 10 for a cardiac patient is illustrated. The garment 10 comprises a shell 20 having a front seam which is closed by closures 12, an interior pocket 14, short sleeves 24 and a belt 22 (see FIG. 2).

The closures 12 of garment 10 are formed of an x-ray penetrable material, such as "VELCRO" brand closures. The remainder of the garment materials are similarly x-ray transparent. The garment 10 includes a row of x-ray penetrable closures 12, which are are placed vertically on the end flaps of the garment 10. The garment thus closes down the front as in other shirt-like garments.

Figure 2:
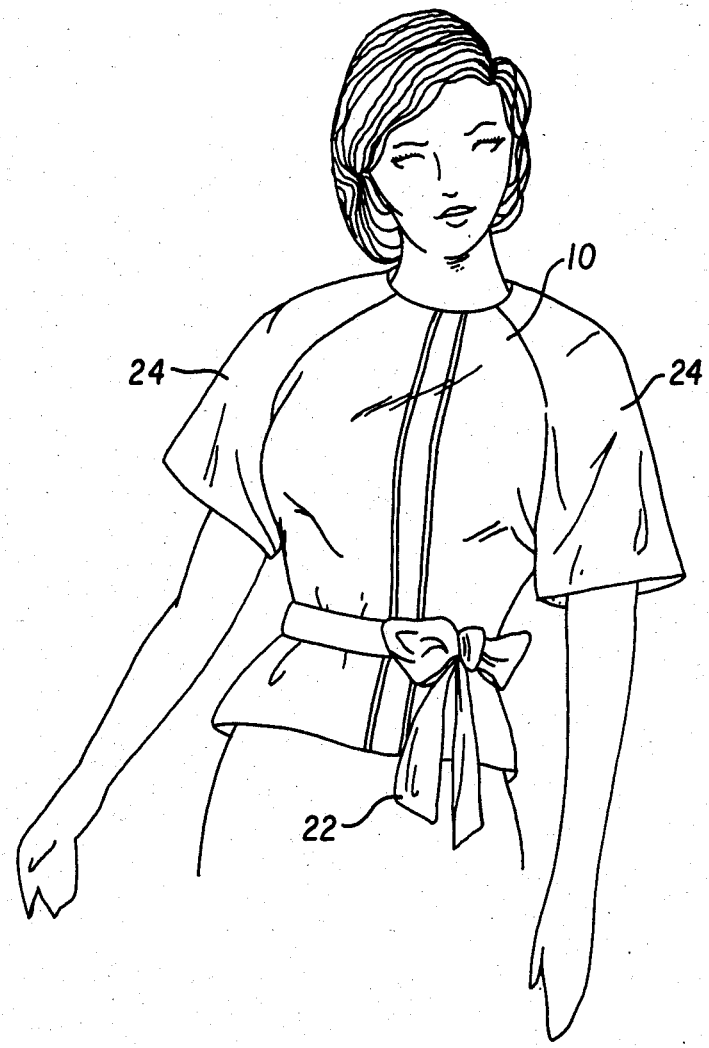
FIG. 2 is a frontal view of the present invention on a patient with the belt in the front-tied position.

The pocket 14 is located on the inside portion of the front of garment 10 on either side, towards the lower edge of the shell. The pocket 14 is of proper size and shape to securely accommodate a cardiac monitor 16. The pocket 14 is located so as to allow electrode wires 26 to be properly connected to conventional electrodes 18. Further, the pocket 14 is located such that a belt 22 (FIGS. 2-3) assists in supporting its weight, thus providing further security, when tied outside the garment to the front over the monitor 16, as shown in FIG. 2. This further security helps to prevent extraneous artifacts (i.e., undesired components in the monitor's output signal) from occurring due to excessive jostling of the monitor 16.

Figure 3:
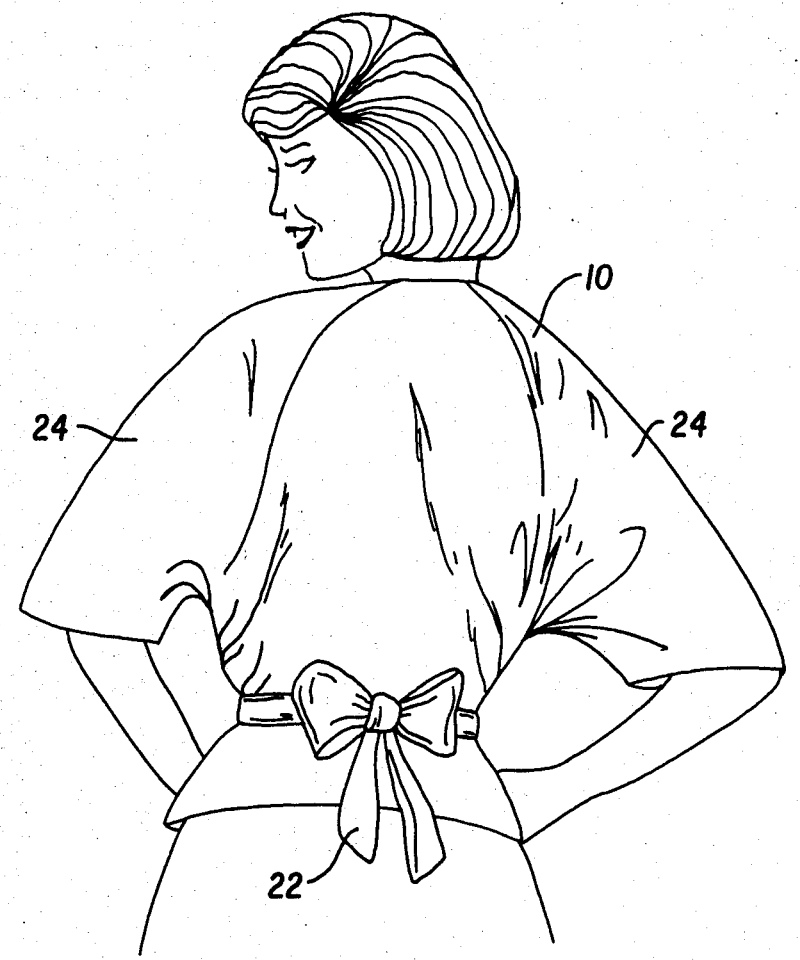
FIG. 3 is a rear view of the present invention with the belt in the rear-tied position.

As shown in FIGS. 2 and 3, the belt 22 is located towards the bottom of garment 10. Each end of belt 22 is fastened on one side of garment 10. This allows belt 22 to be fastened in either the front (FIG. 2) or the back (FIG. 3). Tying in the back is beneficial for securing the monitor when using certain exercise equipment, such as rowing machines, when it is necessary to have any dangling material out of the way. As noted, tying in the front restrains the monitor from moving excessively, which is uncomfortable and which can cause undesirable artifacts in the monitor's output signal. The belt 22, by allowing for selectively adjustable fit, also provides a more attractive appearance and much improved comfort over the typical over-sized, tent-like hospital gowns. In this way, a hospital need not have on hand a wide range of sizes of garments. Of course, several sizes can be provided if desired.

The short sleeves 24 are of such a length as to allow for a blood-pressure cuff, commonly used during stress testing, to be placed on a patient's arm without difficulty. Further, the loose-fitting short sleeves provide maximum comfort.

In normal use, the electrodes 18 are first fastened to the patient's chest, the wires 26 connected to the electrodes and the monitor 16 placed in pocket 14. This can all be accomplished in privacy under the direction of a doctor or a nurse. The patient then closes the garment down the front using the x-ray penetrable closures 12. Typically the belt 22 will be tied across the front of the garment 10 to further restrain movement of the monitor 16 in pocket 14. As mentioned, this helps to prevent extraneous artifacts in the output signal due to excessive jostling of the monitory 16.

Typically, during stress testing, a monitor is not worn, but the patient's blood pressure is monitored. The short sleeves and belt of the garment of the invention allow it to be useful in this connection as well. The short sleeves allow convenient placement of the blood pressure cuff, while the belt allows the garment to fit comfortably to the patient.

In this way an attractive garment, usable by a wide variety of patients (although ultimately provision of, for example, Large and Small sizes might be desirable) and during all of the variety of activities experienced by cardiac patients is provided.

Although the present invention has been described with specific reference to one embodiment, it should be understood that other embodiments can be devised by those skilled in the art. Therefore, the invention should not be considered to be limited by the above exemplary disclosure, but only by the following claims.

What is claimed as new and desired to be secured by letters patent of the United States is:

1. A garment for cardiac patients comprising:
   a hip-length garment shell formed of x-ray penetrable material, having a single openable seam on the front of the shell;
   x-ray penetrable closure means, for closing said seam;
   at least one interior pocket located on one side of the front of said garment shell substantially at waist height for retaining a monitor means; and
   belt means secured to said shell substantially at waist height for securing said monitor means in said pocket and for selectively adjusting the fit of said garment.

2. A garment according to claim 1, wherein said closure means comprises at least one hook and loop closure.

3. A garment according to claim 1, wherein said belt means comprises two straps secured to either side of the garment shell for being tied in front or in back.

4. A garment according to claim 3, further commmprising short sleeves.

5. A garment for cardiac patients comprising:
   a hip-length garment shell having a single openable seam in the front of said shell;
   closure means;
   short sleeves;
   at least one interior pocket located on one side of the front of said shell substantially at waist height for retaining cardiac monitor means; and
   belt means substantially at waist height for securing the monitor means in said pocket and for selectively adjusting the fit of said garment;
   wherein all elements of said garment are x-ray transparent.

6. A garment according to claim 5, wherein said belt means comprises first and second straps secured to said shell on either side of the garment shell for being tied in front or in back of the wearer.

7. A garment according to claim 6, wherein said closure means comprises at least one hook and loop closure.

* * * * *